(12) United States Patent
Packham et al.

(10) Patent No.: US 7,211,246 B2
(45) Date of Patent: May 1, 2007

(54) COMPOSITIONS COMPRISING OESTRONE-3-0-SULPHAMATE AND TRAIL (TNF-RELATED APOPTOSIS INDUCING LIGAND)

(75) Inventors: Keith Graham Packham, Berksire (GB); Michael John Reed, Berksire (GB); Barry Victor Lloyd Potter, Berksire (GB)

(73) Assignee: Sterix Limited, Berkshire (GB)

( * ) Notice: Subject to any disclaimer, the term of this patent is extended or adjusted under 35 U.S.C. 154(b) by 54 days.

(21) Appl. No.: 10/728,383

(22) Filed: Dec. 5, 2003

(65) Prior Publication Data

US 2004/0166090 A1    Aug. 26, 2004

(30) Foreign Application Priority Data

Jun. 7, 2001    (GB) .................. 0113920.3

(51) Int. Cl.
*A61K 45/00*    (2006.01)
*A61K 31/165*    (2006.01)
*C07K 14/52*    (2006.01)

(52) U.S. Cl. .................. 424/85.1; 514/169; 514/171; 514/2; 530/351

(58) Field of Classification Search .................. None
See application file for complete search history.

(56) References Cited

U.S. PATENT DOCUMENTS 5,350,836 A * 9/1994 Kopchick et al. ........... 530/399
6,339,079 B1 * 1/2002 Kasch et al. ................. 514/182

FOREIGN PATENT DOCUMENTS

| WO | WO 97/01633 | 1/1997 |
|----|-------------|--------|
| WO | WO 99/64013 | 12/1999 |
| WO | 2000/66095 | 11/2000 |
| WO | WO 00/66095 | 11/2000 |
| WO | 2002/16394 | 2/2002 |
| WO | 2004/085459 | 10/2004 |

OTHER PUBLICATIONS

Gura, T. Science, vol. 278, Nov. 1997, pp. 1041-1042.*
Gerald Dermer, Bio/Technology, Mar. 1994, vol. 12, p. 320.*
Rakesh Jain, Science, Feb. 23, 1996, vol. 271.*
Rakesh Jian, Cancer and Metastasis Revies, 1990, vol. 9, pp. 253-266.*
Francklyn, C., Aminoacyl-tRNA Synthetases: Versatile Players in the Changing Theater of Translation, RNA, vol. 8, pp. 1363-1372 (2002).*
Goodman & Gilman's The Pharmacological Basis of Therapeutics, 9th Ed., McGraw-Hill, NY, (1996).*
Nagase, H., et al., The Pharmacological Profile of δ Opioid Receptor Ligands, (+) and (−) TAN-67 on Pain Modulation, Life Sciences, vol. 68, pp. 2227-2231 (2001).*
Kick, E.K., et al., Structure-Based Design and Combinatorial Chemistry Yield Low Nanomolar Inhibitors of Cathepsin D, Chemistry & Biology, vol. 4, No. 4, pp. 297-307 (1997).*
Elger, W., et al., J. Ster. Biochem. Molec. Biol. 55 (1995) 395-403.*
MacCarthy, L. et al., "Differential Effects of Estrone and Estrone-3-O-Sulfamate Derivatives on Mitotic Arrest, Apoptosis, and Mirctubule Assembly in Human Breast Cancer Cells," *Cancer Research*, 60: 5441-50, 2000 (XP-001031282).
Pitti, R. et al., "Induction of Apoptosis by Apo-2-Ligand, a New Member of the Tumor Necrosis Factor Cytokine Family," *Journal of Biological Chemistry*, 271(22): 12687-90, 1996 (XP-002031265).
Purohit, A. et al., "The Development of A-ring Modified Analogues of Oestrone-3-O-sulphamate as Potent Steroid Sulphatase Inhibitors with Reduced Oestrogenicity," *J. Steroid Biochem. Molec. Biol.*, 64(5-6): 269-75, 1998 (XP-000852539).
Purohit, A. et al., "The Effect of 2-Methoxyoestrone-3-O-Sulphamate on the Growth of Breast Cancer Cells and Induced Mammary Tumours," *Int. J. Cancer*, 85: 584-89, 2000 (XP-001039923).
Spyridopoulos, I. et al., "Restoration of E2F Expression Rescues Vascular Endothelial Cells from Tumor Necrosis Factor-α-Induced Apoptosis," *Circulation*, 98:2883-90, 1998 (XP-002214772).
Wiley, S. et al., "Identification and Characterization of a New Member of the TNF Family that Induces Apoptosis," *Immunity*, 3: 673-82, 1995 (XP-000672297).
Reed, M.J. et al. "Steroid Sulfatase: Molecular Biology, Regulation and Inhibition." Endocrine Reviews2005; 26:171-202.

* cited by examiner

Primary Examiner—Eileen B. O'Hara
(74) *Attorney, Agent, or Firm*—Frommer Lawrence & Haug LLP; Thomas J. Kowalski; Angela M. Collison

(57) ABSTRACT

The present invention provides a composition comprising (i) a compound comprising a sulphamate group ("a sulphamate compound"); and (ii) an apoptosis inducer.

16 Claims, 10 Drawing Sheets

COMPOSITIONS COMPRISING OESTRONE-3-0-SULPHAMATE AND TRAIL (TNF-RELATED APOPTOSIS INDUCING LIGAND)

The present invention relates to a composition. In particular the present invention relates to a pharmaceutical composition and to a use thereof.

Cancer remains a major cause of mortality in most Western countries. So far, evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore specific inhibitors of oestrogen biosynthesis are of potential value for the treatment of endocrine-dependent tumours.

Over the past two decades, there has been considerable interest in the development of inhibitors of the aromatase pathway which converts the androgen precursor androstenedione to oestrone. However, there is now evidence that the oestrone sulphatase ("E1-STS") pathway, i.e. the hydrolysis of oestrone sulphate ("E1S") to oestrone ("E1"), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione and also by the fact that plasma E1S concentration in these aromatase inhibitor-treated patients remains relatively high. The long half-life of E1S in blood (10–12 h) compared with the unconjugated oestrogens (20 min) and high levels of steroid sulphatase activity in liver and, normal and malignant breast tissues, also lend support to this theory.

Singh et al (1997 J Steroid Biochem Mol Biol 61: 185–192), report that the major source of pro-inflammatory cytokines, such as TNF-α and IL-6 within breast tumours is not well understood but it is thought that tumour infiltrating macrophages and lymphocytes might play a role.

Singh et al (ibid) also report that both TNF-α and IL-6 inhibit the growth of MCF-7 breast cancer cells in vitro. In addition, TNF-α has an inhibitory effect on aromatase activity measured in cultured MCF-7 breast cancer cells. Apparently, these results contrast with the marked stimulatory effect that TNF-α has on fibroblasts derived from normal and malignant breast tissues (Macdiarmaid et al 1994 Molec. Cell Endoc. 106: 17–21). In addition, when TNF-α is combined with IL-6, the inhibitory effect on aromatase activity is enhanced. The synergistic inhibitory effect of IL-6 and TNF-α on aromatase activity in MCF-7 cells also contrasts to the synergistic stimulatory effect that these cytokines have on oestrone sulphatase and oestradiol dehydrogenase activities in these cells.

Tumour necrosis factor (TNF) related apoptosis inducing ligand (TRAIL/Apo-2L) induces apoptosis in a wide range of tumour cells by binding to the receptors TRAIL-R1 (DR4) and TRAIL-R2 (DR5). These are members of the TNFα superfamily of death receptors, characterised by the possession of intracellular 'death domains', that are responsible for transduction of the death signal (Ashkenazi and Dixit 1998).

Treatment with TRAIL in combination with DNA damaging agents such as doxorubicin, etoposide and ionising radiation has been shown to significantly enhance the antitumour actions of TRAIL in breast cancer cells (Keane et al., 1999, Gibson et al., 2000, Chinnalyan et al., 2000). The mechanism for this co-operation is thought to be due to the ability of DNA damaging agents to increase levels of DR5 and/or DR4 receptors, possibly mediated through upregulation of the tumour suppressor p53 or the transcription factor NFκB. (Wu et al., 1997, Gibson et al., 2000).

The present invention seeks to provide a composition suitable for use in the treatment of cancers and, especially, breast cancer.

According to a first aspect of the present invention there is provided a composition comprising (i) a compound comprising a sulphamate group ("a sulphamate compound"); and (ii) an apoptosis inducer.

According to a second aspect of the present invention there is provided a composition of the present invention for use in medicine.

According to a third aspect of the present invention there is provided a use of a composition of the present invention in the manufacture of a medicament to prevent and/or inhibit tumour growth.

According to a fourth aspect of the present invention there is provided a use of a composition of the present invention a composition of the present invention in the manufacture of a medicament to induce apoptosis.

According to a fifth aspect of the present invention there is provided a use of a sulphamate compound in the manufacture of a medicament to upregulate receptor function of a tumour necrosis factor apoptosis inducing ligand (TRAIL) receptor.

According to a sixth aspect of the present invention there is provided a method of treatment comprising administering to a subject in need of treatment a composition of the present invention.

According to a seventh aspect of the present invention there is provided a method of treatment comprising administering to a subject in need of treatment a composition of the present invention or an sulphamate compound in order to induce apoptosis.

According to an eighth aspect of the present invention there is provided a kit comprising a part i) containing a compound comprising a sulphamate group ("a sulphamate compound"); and a part ii) containing an apoptosis inducer. The parts of the kit may be independently held in one or more containers—such as bottles, syringes, plates, wells, blister pack etc.

According to a ninth aspect of the present invention there is provided a use of a composition of the present invention in the manufacture of a medicament to activate a caspase.

According to a tenth aspect of the present invention there is provided a use of a sulphamate compound in the manufacture of a medicament to activate a caspase.

The present invention is advantageous in that it provides a composition suitable for use in the treatment of cancers and, especially, breast cancer.

In addition, the present invention is advantageous in that it provides a compound that is suitable for use in the treatment of cancers such as breast cancer, ovarian cancer, endometrial cancer, sarcomas, melanomas, prostate cancer etc.—especially, breast cancer.

Another advantage of the compositions of the present invention is that they may be more potent in vivo than the sulphamate compounds alone or the apoptosis inducer alone. Moreover, in some aspects the combination of sulphamate compounds and the apoptosis inducer is more potent than one would expect from the potency of the compound alone i.e. this is a synergistic relationship between them.

The synergistic combination of sulphamate compound and apoptosis inducer allows for the use of lower doses of either or both of the sulphamate compound and apoptosis inducer. This is particularly advantageous when therapeutic amounts required in non-synergistic systems are to be avoided, for example for reasons of toxicity of one of the components.

We have surprisingly found that the sulphamate compounds of the present invention upregulate receptor function of a tumour necrosis factor apoptosis inducing ligand (TRAIL) receptor. In one aspect by the term "upregulate receptor function" it is meant that increased signalling via the receptor is provided. Without being bound by theory it is believed that present compounds may remove or inhibit agents which would otherwise reduce or themselves inhibit the receptor. It may be said that the compounds of the invention sensitise the tumour necrosis factor apoptosis inducing ligand (TRAIL) receptor to TRAIL.

In accordance with the present invention the composition of the present invention may comprise more than one apoptosis inducer.

Preferably, the apoptosis inducer is an apoptosis inducing ligand.

Preferably, the apoptosis inducer is an apoptosis inducing cytokine.

A cytokine is a molecule—often a soluble protein—that allows immune cells to communicate with each other. These molecules exert their biological functions through specific receptors expressed on the surface of target cells. Binding of the receptors triggers the release of a cascade of biochemical signals which profoundly affect the behaviour of the cell bearing the receptor (Poole, S 1995 TibTech 13: 81–82). Many cytokines and their receptors have been identified at the molecular level (Paul and Sedar 1994, Cell 76: 241–251) and make suitable molecules of therapeutic value as well as therapeutic targets in their own right.

More details on cytokines can be found in Molecular Biology and Biotechnology (Pub. VCH, Ed. Meyers, 1995, pages 202, 203, 394, 390, 475, 790).

More preferably the cytokine is a tumour necrosis factor apoptosis inducing ligand (TRAIL). Yet more preferably the TRAIL is TRAIL/Apo-2L.

With this aspect of the present invention the compositions of the present invention are more potent in vivo than the sulphamate compounds alone or TRAIL alone. Moreover, in some aspects the combination of sulphamate compounds and TRAIL is more potent than one would expect from the potency of the compound alone i.e. this is a synergistic relationship between them.

The TRAIL can be prepared chemically or it can be extracted from sources. Preferably, the TRAIL is prepared by use of recombinant DNA techniques.

In a preferred aspect the apoptosis inducer is capable of interacting with a tumour necrosis factor apoptosis inducing ligand (TRAIL) receptor. Preferably the receptor is DR4 and/or DR5.

In one aspect the present invention may be used for the activation of a caspase.

By the term caspase it is typically meant a caspase family protease. The term "caspase family protease" is intended to include members of the caspase proteases as described in Alnemri, E. et al. (1996) Cell 87:171, including caspase-1 (ICE), caspase-2 (ICH-1), caspase-3 (CPP32, Yama, apopain), caspase-4 (TX, ICH-2, ICE.sub.rel-II), caspase-5 (ICE.sub.rel-III, TY), caspase-6 (Mch2), caspase-7 (Mch3, ICE-LAP3, CMH-1), caspase-8 (MACH, FLICE, Mch5), caspase-9 (ICE-LAP6, Mch6) and caspase-10 (Mch4). Furthermore, a "caspase family protease" is intended to include any protein that shares greater than 20% amino acid sequence identity with ICE in the active domains of the protease (i.e., active domains of the p10 and p20 subunits of ICE), contains the peptide sequence glutamine-alanine-cysteine-X-glycine (QACXG), wherein the cysteine (C) is the catalytically active cysteine residue and X denotes any amino acid, and contains the sequence serine-histidine-glycine (SHG), located N-terminal to the QACXG motif, in which the histidine (H) is the catalytically essential histidine residue. Caspase family proteases typically demonstrate a strong preference for hydrolysis of peptide bonds immediately following an acidic amino acid (i.e., aspartic acid or glutamic acid).

Caspase family proteases are known in humans and other organisms including mice and *Caenorhabditis elegans*. Examples of caspase family proteases include, for example, Ich-1 (Wang, L. et al. (1994) Cell 78:739–750); ICH-2 (Kamens, J. et al. (1995) J. Biol. Chem. 270:15250–15256); Mch2 (Fernandes-Alnemri, T. et al. (1995) Cancer Res. 55:2737–2742); CPP32 (Fernandes-Alnemri, T. et al. (1994) J. Biol. Chem. 269:30761–30764); Yama/CPP32.beta. (Tewari, M. et al. (1995) Cell 81:801–809); the product of the mouse gene Nedd2 (Kumar, S. et al. (1992) Biochem. Biophys. Res. Commun. 185:1155–1161; Kumar, S. et al. (1994) Genes Dev. 8:1613–1626); the product of the *C. elegans* gene, ced-3 (Yuan, J. et al. (1993) Cell 75:641–652); the human protein TX (Faucheu, C., et al., (1995) EMBO J. 14:1914–1922); ICE.sub.rel II and ICE.sub.rel III (Munday, N. A. et al. (1995) J. Biol. Chem. 270:15870–15876).

Preferably the caspase is an effector caspase.

Preferably the caspase is caspase 3.

In accordance with the present invention the composition of the present invention may comprise more than one sulphamate compound.

The term "sulphamate compound" means a compound comprising at least one sulphamate group.

The term "sulphamate" includes an ester of sulphamic acid, or an ester of an N-substituted derivative of sulphamic acid, or a salt thereof.

Preferably, the sulphamate group of the sulphamate compound has the formula:

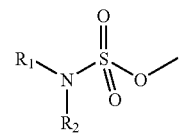

wherein each of $R_1$ and $R_2$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably, $R_1$ and $R_2$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl, N-acyl, or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—$PhCH_3$; o-, m- or p-). Where $R_1$ and $R_2$ represent cycloalkyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. —O— or —NH— to provide a 1,6- or 7-membered heterocycle, e.g. morpholino, pyrrolidino or piperidino.

Within the values alkyl, cycloalkyl, alkenyl, acyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl. A non-limiting example of a hydrocarbyl group is an acyl group.

In some preferred embodiments, at least one of $R_1$ and $R_2$ is H.

Preferably the sulphamate compound is a cyclic compound. In this regard, the sulphamate compound can be a single ring compound or a polycyclic compound. Here, the term "polycyclic" includes fused and non-fused ring structures including combinations thereof.

Thus, preferably the sulphamate compound is of the formula

E-G wherein E is a sulphamate group and wherein G is a cyclic group.

The cyclic group may be a single ring or it is a polycyclic ring structure.

In one aspect, the cyclic group may contain any one or more of C, H, O, N, P, halogen (including Cl, Br and I), S and P.

At least one of the cyclic groups may be a heterocyclic group (a heterocycle) or a non-heterocyclic group.

At least one of the cyclic groups may be a saturated ring structure or an unsaturated ring structure (such as an aryl group).

Preferably, at least one of the cyclic groups is an aryl ring.

Preferably, the sulphamate group is linked to the aryl ring.

If the cyclic group is polycyclic some or all of the ring components of the sulphamate compound may be fused together or joined via one or more suitable spacer groups.

Thus, in accordance with one aspect of the present invention, preferably the sulphamate compound is a polycyclic compound. In this aspect the sulphamate compound may be a compound having the formula

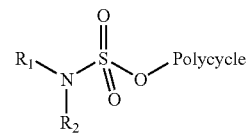

wherein each of $R_1$ and $R_2$ is independently selected from H or a hydrocarbyl group.

Preferably the polycyclic compound will contain, inclusive of all substituents, no more than 50 about carbon atoms, more usually no more than about 30 to 40 carbon atoms.

The polycyclic compound can comprise at least two ring components, or least three ring components, or least four ring components.

Preferably, the polycyclic compound comprises four ring components.

Preferred polycyclic compounds have a steroidal ring component—that is to say a cyclopentanophenanthrene skeleton, or bio-isosteres thereof.

As is well known in the art, a classical steroidal ring structure has the generic formula of:

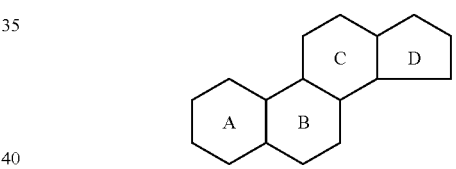

In the above formula, the rings have been labelled in the conventional manner.

When the sulphamate compound has a steroidal ring component the compound may be a compound having the formula

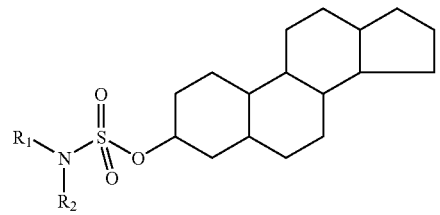

wherein each of $R_1$ and $R_2$ is independently selected from H or a hydrocarbyl group.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic compound can be presented as:

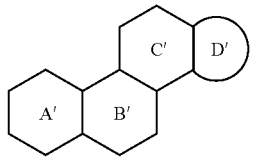

wherein each ring A', B', C' and D' independently represents a heterocyclic ring or a non-heterocyclic ring, which rings may be independently substituted or unsubstituted, saturated or unsaturated.

By way of example, any one or more of rings A', B', C' and D' may be independently substituted with suitable groups—such as an alkyl group, an allyl group, an hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms may be present in the ring.

Examples of suitable, preferred steroidal nuclei rings A'–D' of the compounds of the present invention include rings A–D of oestrone and dehydroepiandrosterone.

Preferred steroidal nuclei rings A'–D' of the compounds of the present invention include rings A–D of:

Oestrones and Substituted Oestrones, viz:
oestrone
2-OH-oestrone
2-alkoxy-oestrone (such as $C_{1-6}$ alkoxy-oestrone, such as 2-methoxy-oestrone)
2-alkyl-oestrone (such as $C_{1-6}$ alkyl-oestrone, such as 2-ethyl-oestrone)
4-OH-oestrone
6α-OH-oestrone
7α-OH-oestrone
16α-OH-oestrone
16βH-oestrone Oestradiols and Substituted Oestradiols, viz:
2-OH-17β-oestradiol
2-alkoxy-17β-oestradiol (such as $C_{1-6}$ alkoxy-17β-oestradiol, such as 2-methoxy-17β-oestradiol)
2-alkyl-17β-oestradiol (such as $C_{1-6}$ alkyl-17β-oestradiol, such as 2-ethyl-17β-oestradiol)
4-OH-17β-oestradiol
6α-OH-17β-oestradiol
7α-OH-17β-oestradiol
2-OH-17α-oestradiol
2-alkoxy-17α-oestradiol (such as $C_1$ alkoxy-17α-oestradiol, such as 2-methoxy-17α-oestradiol)
2-alkyl-17α-oestradiol (such as $C_{1-6}$ alkyl-17α-oestradiol, such as 2-ethyl-17α-oestradiol)
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol Oestriols and Substituted Oestriols, viz:
oestriol
2-OH-oestriol
2-alkoxy-oestriol (such as $C_{1-6}$ alkoxy-oestriol, such as 2-methoxy-oestriol)
2-alkyl-oestriol (such as $C_{1-6}$ alkyl-oestriol, such as 2-ethyl-oestriol)
4-OH-oestriol
6α-OH-oestriol
7α-OH-oestriol Dehydroepiandrosterones and Substituted Dehydroepiandrosterones, viz:
dehydroepiandrosterones
6α-OH-dehydroepiandrosterone
7α-OH-dehydroepiandrosterone
16α-OH-dehydroepiandrosterone
16β-OH-dehydroepiandrosterone In general terms the ring system A'B'C'D' may contain a variety of non-interfering substituents. In particular, the ring system A'B'C'D' may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

In an alternative embodiment, the polycyclic compound may not contain or be based on a steroid nucleus. In this regard, the polycyclic compound may contain or be based on a non-steroidal ring system—such as diethylstilboestrol, stilboestrol, coumarins, and other ring systems. Other suitable non-steroidal compounds for use in or as the composition of the present invention may be found in U.S. Pat. No. 5,567,831.

In a preferred aspect the at least one sulphamate group is attached to any one or more of the ring components of a cyclic compound.

Preferably, the polycyclic compound has a steroidal structure and wherein the sulphamate group is attached to the A ring.

Preferably, the sulphamate group is attached to the 3 position of the A ring.

In some embodiments, the compound of the invention may contain more than one sulphamate group, such as at least two sulphamate groups. By way of example, there may be two sulphamates (i.e. bis-sulphamate compounds). If these compounds are based on a steroidal nucleus, preferably the second (or at least one of the additional) sulphamate group is located at position 17 of the steroidal nucleus. The more than one sulphamate groups need not be the same.

Preferably the sulphamate compound comprises at least one hydrocarbyl group or oxyhydrocarbyl group. The hydrocarbyl group or oxyhydrocarbyl group are referred to herein as a (oxy)hydrocarbyl group.

In a preferred embodiment the (oxy)hydrocarbyl group and the sulphamate group are each attached to the same ring at positions ortho with respect to each other.

A preferred sulphamate compound is an (oxy)hydrocarbyl steroidal sulphamate compound (i.e. a sulphamate compound comprising a steroidal component and an (oxy)hydrocarbyl group). In this aspect preferably the (oxy)

hydrocarbyl group and the sulphamate group are each attached to the A ring of the steroidal structure/component.

In respect of steroidal embodiments of the invention preferably the (oxy)hydrocarbyl group is attached to the 2 position of the A ring of the steroidal structure and/or the sulphamate group is attached to the 3 position of the A ring of the steroidal structure. In one embodiment, preferably, the sulphamate compound is an (oxy)hydrocarbyl steroidal sulphamate compound wherein the sulphamate group is in the 3 position on the steroidal component and/or the (oxy)hydrocarbyl group is in the 2-position position on the steroidal component.

In one embodiment, preferably, the sulphamate compound is an oxyhydrocarbyl derivative of oestrone sulphamate.

In one embodiment, preferably, the sulphamate compound is an oxyhydrocarbyl derivative of oestrone-3-O-sulphamate.

In one embodiment, preferably, the sulphamate compound is a $C_{1-6}$ (such as a $C_{1-3}$) alkoxy or alkyl derivative of oestrone-3-O-sulphamate.

In one embodiment, preferably, the sulphamate compound is a 2-$C_{1-6}$ (such as a $C_{1-3}$) alkoxy or alkyl derivative of oestrone-3-O-sulphamate.

The term "oxyhydrocarbyl group" as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one preferred embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably, the (oxy)hydrocarbyl group is an alkoxy/alkyl. The alkyl group (of the alkoxy substituent) is preferably a lower alkyl group containing from 1 to 5 carbon atoms, that is to say methyl, ethyl, propyl etc. Preferably, the alkyl group is methyl or ethyl.

In one embodiment, preferably the oxyhydrocarbyl group is a group of the formula $C_{1-6}O$ (such as a $C_{1-3}O$), more preferably a methoxy group.

More preferably the group $C_{1-6}O$ is attached to the 2 position of the A ring of a steroidal nucleus.

In a highly preferred embodiment the sulphamate compound is 2-methoxyoestrone-3-O-sulphamate.

In one embodiment, preferably the hydrocarbyl group is a group of the formula $C_{1-6}$, more preferably an ethyl group.

In a highly preferred embodiment the sulphamate compound is 2-ethyloestrone-3-O-sulphamate.

If the sulphamate compound comprises a steroidal nucleus, preferably the A ring has an (oxy)hydrocarbyl group at the 2 position.

Preferably the sulphamate compound comprises at least one sulfanylhydrocarbyl group. By the term sulfanylhydrocarbyl it is meant a group of the formula -L-S—R, wherein L is an optional linker group, S represents sulphur and R is a hydrocarbyl group (as defined herein).

In a preferred embodiment the sulfanylhydrocarbyl group and the sulphamate group are each attached to the same ring at positions ortho with respect to each other.

A preferred sulphamate compound is an sulfanylhydrocarbyl steroidal sulphamate compound (i.e. a sulphamate compound comprising a steroidal component and an sulfanylhydrocarbyl group). In this aspect preferably the sulfanylhydrocarbyl group and the sulphamate group are each attached to the A ring of the steroidal structure/component.

In respect of steroidal embodiments of the invention preferably the sulfanylhydrocarbyl group is attached to the 2 position of the A ring of the steroidal structure and/or the sulphamate group is attached to the 3 position of the A ring of the steroidal structure. In one embodiment, preferably, the sulphamate compound is an sulfanylhydrocarbyl steroidal sulphamate compound wherein the sulphamate group is in the 3 position on the steroidal component and/or the sulfanylhydrocarbyl group is in the 2-position position on the steroidal component.

In one embodiment, preferably, the sulphamate compound is an sulfanylhydrocarbyl derivative of oestrone sulphamate.

In one embodiment, preferably, the sulphamate compound is an sulfanylhydrocarbyl derivative of oestrone-3-O-sulphamate.

In one embodiment, preferably, the sulphamate compound is a $C_{1-6}$ (such as a $C_{1-3}$) alkyl sulfanyl derivative of oestrone-3-O-sulphamate.

In one embodiment, preferably, the sulphamate compound is a 2-$C_{1-6}$ (such as a $C_{1-3}$) alkyl sulfanyl derivative of oestrone-3-O-sulphamate.

In one preferred embodiment of the present invention, the sulfanylhydrocarbyl group is a sulfanylhydrocarbon group.

By the term "sulfanylhydrocarbon" it is meant a group of the formula -L-S—R, wherein L is an optional linker group, S represents sulphur and R is a hydrocarbon group (as defined herein).

In one embodiment, preferably the sulfanylhydrocarbyl group is a group of the formula $C_{1-6}S$ (such as a $C_{1-3}S$), more preferably a $CH_3S$ or $CH_3CH_2S$ group.

More preferably the group $C_{1-6}S$ is attached to the 2 position of the A ring of a steroidal nucleus.

In a highly preferred embodiment the sulphamate compound is 2-methylsulfanyloestrone-3-O-sulphamate or 2-ethylsulfanyloestrone-3-O-sulphamate.

Preferably, if the sulphamate group on the sulphamate compound were to be replaced with a sulphate group to form a sulphate compound then the sulphate compound would be hydrolysable by a steroid sulphatase enzyme (E.C.3.1.6.2).

Preferably if the sulphamate group on the sulphamate compound were to be replaced with a sulphate group to form a sulphate compound and the sulphate compound were to be incubated with a steroid sulphatase enzyme (E.C.3.1.6.2) at a pH 7.4 and 37° C. it would provide a $K_m$ value of less than 50 mM.

Preferably if the sulphamate group on the sulphamate compound were to be replaced with a sulphate group to form a sulphate compound and the sulphate compound were to be incubated with a steroid sulphatase enzyme (E.C.3.1.6.2) at a pH 7.4 and 37° C. it would provide a $K_m$ value of less than 50 µM.

Preferably the sulphamate compound is suitable for use as an inhibitor of oestrone sulphatase (E.C. 3.1.6.2).

In one preferred embodiment of the present invention, preferably the sulphamate compound is non-oestrogenic. The term "non-oestrogenic" means exhibiting no or substantially no oestrogenic activity.

In one preferred embodiment of the present invention, preferably the sulphamate compound are not capable of being metabolised to compounds which display or induce hormonal activity.

In one preferred embodiment of the present invention, preferably the composition of the present invention is orally active.

The present invention is based on the highly surprising finding that the combination of a sulphamate compound and a apoptosis inducer provides an effective treatment of cancer.

More in particular, we have surprisingly found that the composition of the present invention can induce apoptosis.

We have identified that in some aspects it may not be necessary for the compound to be a sulphamate compound. Thus in a further aspect the present invention provides a composition comprising (i) a steroidal compound; and (ii) an apoptosis inducer. In this aspect the preferred features of the an apoptosis inducer and steroid nucleus of sulphamate compound described above equally apply to the composition comprising the steroidal compound and apoptosis inducer. The composition comprising (i) a steroidal compound; and (ii) an apoptosis inducer may be utilised in each of the uses and methods described herein.

Apoptosis is induced by microtubule-targeting drugs, a process which may involve the phosphorylation (and inactivation) of the apoptosis regulator, the bcl-2 protein (Halder, Cancer Res. 57: 229, 1997).

Preferably the composition of the present invention further comprises a pharmaceutically acceptable carrier, diluent, or excipient.

For pharmaceutical administration, the composition of the present invention can be formulated in any suitable manner utilising conventional pharmaceutical formulating techniques and pharmaceutical carriers, adjuvants, excipients, diluents etc.—such as those for parenteral administration. Approximate effective dose rates are in the range 100 to 800 mg/day depending on the individual activities of the compounds in question and for a patient of average (70 Kg) bodyweight. More usual dosage rates for the preferred and more active compositions will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of composition per unit dose. Alternatively and preferably the compositions will be formulated for parenteral administration in a suitable parenterally administrable carrier and providing single daily dosage rates in the range 10 to 800 mg, 10 to 500 mg, 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

The composition or compound of the present invention may be administered in any suitable manner—such as any one or more of oral administration, topical administration (such as by means of a patch), parenteral administration, rectal administration or by inhalation spray.

In the method of treatment, the subject is preferably a mammal, more preferably a human. For some applications, preferably the human is a woman.

For particular applications, it is envisaged that the compositions of the present invention may be used in combination therapies, either with another sulphatase inhibitor, or, for example, in combination with an aromatase inhibitor, such as for example, 4-hydroxyandrostenedione (4-OHA).

In accordance with the present invention, the components of the composition can be added in admixture, simultaneously or sequentially. Furthermore, in accordance with the present invention it may be possible to form at least a part of the composition in situ (such as in vivo) by inducing the expression of—or increasing the expression of—one of the components. For example, it may be possible to induce the expression of—or increase the expression of—the apoptosis inducer, such as TNF. By way of example, it may be possible to induce the expression of—or increase the expression of—TNF by adding bacterial lipopolysaccharide (LPS) and muramyl dipeptide (MDP). In this regard, bacterial LPS and MDP in combination can stimulate TNF production from murine spleen cells in vitro and tumour regression in vivo (Fuks et al Biull Eksp Biol Med 1987 104: 497–499).

Examples of suitable sulphamate compounds for use in or as the composition of the present invention, or examples of suitable compounds that can be converted to suitable sulphamate compounds for use in or as the composition of the present invention, can be found in the art—such as PCT/GB92/01587, PCT/GB97/03352, PCT/GB97/00444, GB 9725749.7, GB 9725750.5, U.S. Pat. Nos. 5,567,831, 5,677, 292, 5,567,831, WO-A-96/05216, and WO-A-96105217.

By way of example, PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters. Examples of such inhibitors are sulphamate ester derivatives of steroids.

A compound suitable for use in the present invention—which is also a preferred compound of PCT/GB92/01587—is oestrone-3-sulphamate (otherwise known as "EMATE"), which has the following structure:

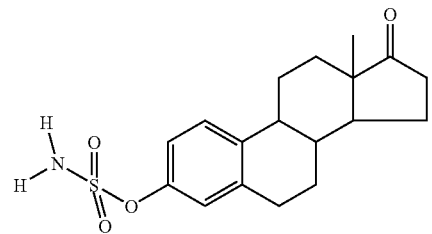

It is known that EMATE is a potent E1-STS inhibitor as it displays more than 99% inhibition of E1-STS activity in intact MCF-7 cells at 0.1 µM. EMATE also inhibits the E1-STS enzyme in a time- and concentration-dependent manner, indicating that it acts as an active site-directed inactivator.

Preferably, the A ring has a substituent that is an (oxy) hydrocarbyl group.

Another compound suitable for use in the present invention has at least the following skeletal structure:

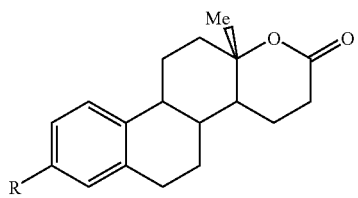

wherein R denotes a sulphamate group as described above.

Preferably, R is the above-mentioned preferred formula for the sulphamate group. In this regard, it is preferred that at least one of $R_1$ and $R_2$ is H.

Preferably, the A ring has a substituent that is an (oxy) hydrocarbyl group.

Another compound suitable for use in the present invention has at least the following skeletal structure:

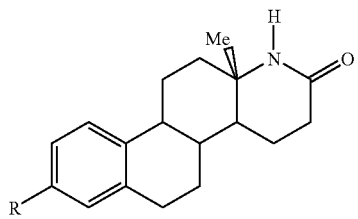

wherein R denotes a sulphamate group as described above.

Preferably, R is the above-mentioned preferred formula for the sulphamate group. In this regard, it is preferred that at least one of $R_1$ and $R_2$ is H.

Preferably, the A ring has a substituent that is an (oxy) hydrocarbyl group.

In accordance with a preferred aspect of the present invention, if the sulphamate group of the compound were to be replaced with a sulphate group to form a sulphate compound then that sulphate compound would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 mM when incubated with steroid sulphatase EC 3.1.6.2 at pH 7.4 and 37° C.

In another preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a $K_m$ value of less than 50 μM when incubated with steroid sulphatase EC 3.1.6.2 at pH 7.4 and 37° C.

In a further aspect the present invention provides use of a sulphamate compound for the manufacture of a medicament to prevent and/or inhibit tumour growth; wherein the sulphamate compound is suitable for use as an inhibitor of oestrone sulphatase (E.C. 3.1.6.2); wherein the compound is a polycyclic compound having a steroidal structure, or a bio-isostere thereof; wherein the polycyclic compound comprises at least one sulphamate group attached to the A ring; and wherein the polycyclic compound comprises at least one oxyhydrocarbyl group attached to the A ring.

We have found that sulphamate compounds to upregulate receptor function of a tumour necrosis factor apoptosis inducing ligand (TRAIL) receptor.

Thus in a further aspect the present invention provides use of a sulphamate compound in the manufacture of a medicament to upregulate to upregulate receptor function of a tumour necrosis factor apoptosis inducing ligand (TRAIL) receptor.

A preferred sulphamate compound of the present invention has the formula:

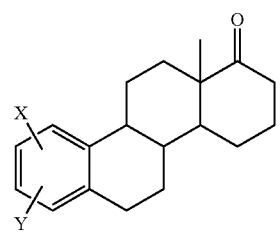

wherein X is an (oxy)hydrocarbyl group; and Y is a sulphamate group; and wherein rings A, B, C and D are independently optionally substituted.

Preferably Y is in the 3-position.

Preferably X is in the 2-position.

For the present invention, preferably the sulphamate compound is an oxyhydrocarbyl steroidal sulphamate compound, in particular 2-methoxyoestrone-3-O-sulphamate, 2-ethyloestrone-3-O-sulphamate, or 2-methoxyoestrone-3-O,17-bissulphamate or a pharmaceutically active salt thereof, including analogues thereof.

2-methoxyoestrone-3-O-sulphamate is an analogue of EMATE—and can be called 2-methoxy EMATE (2-MeOE-MATE). 2-ethyloestrone-3-O-sulphamate is an analogue of EMATE—and can be called 2-ethyl EMATE (2-EtEMATE). 2-methoxyoestrone-3-O,17-bissulphamate is an analogue of EMATE—and can be called MeOE2bisMATE. 2-MeOE-MATE and 2-EtEMATE are described in detail in WO 99/64013 and WO 00/66095, respectively. 2-MeOE2bisMATE is described in detail in WO 02/16392 (PCT/GB01/03688).

2-methoxy EMATE has the formula presented as formula below:

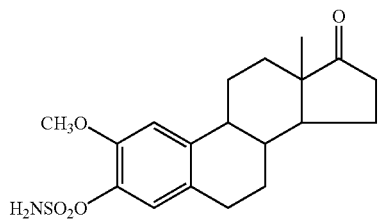

2-ethyl EMATE has the formula presented as formula below:

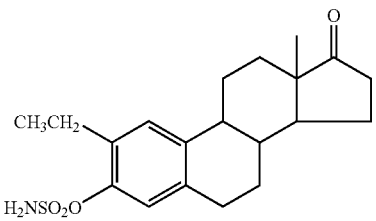

2-MeOE2bisMATE has the formula presented as formula below:

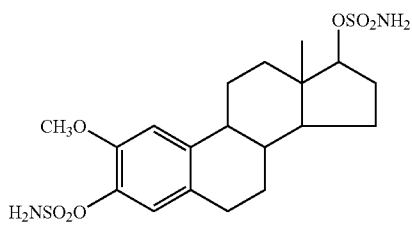

The sulphamate compounds of the present invention may be prepared by reacting an appropriate alcohol with the appropriate sulfamoyl chloride, $R_1R_2NSO_2Cl$. Preferred conditions for carrying out the reaction are as follows. Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography. Preferably, the alcohol is derivatised, as appropriate, prior to reaction with the sulfamoyl chloride. Where necessary, functional groups in the alcohol may be protected in known manner and the protecting group or groups removed at the end of the reaction.

In a further aspect of the present invention there is provided a use of a sulphamate compound in the manufacture of a medicament to upregulate a tumour necrosis factor apoptosis inducing ligand (TRAIL) receptor.

In summation, the present invention provides compositions for use in treatment of tumours and pharmaceutical compositions containing them.

The present invention will now be described only by way of example, in which reference, in which reference shall be made to the following Figures.

Figure 3:
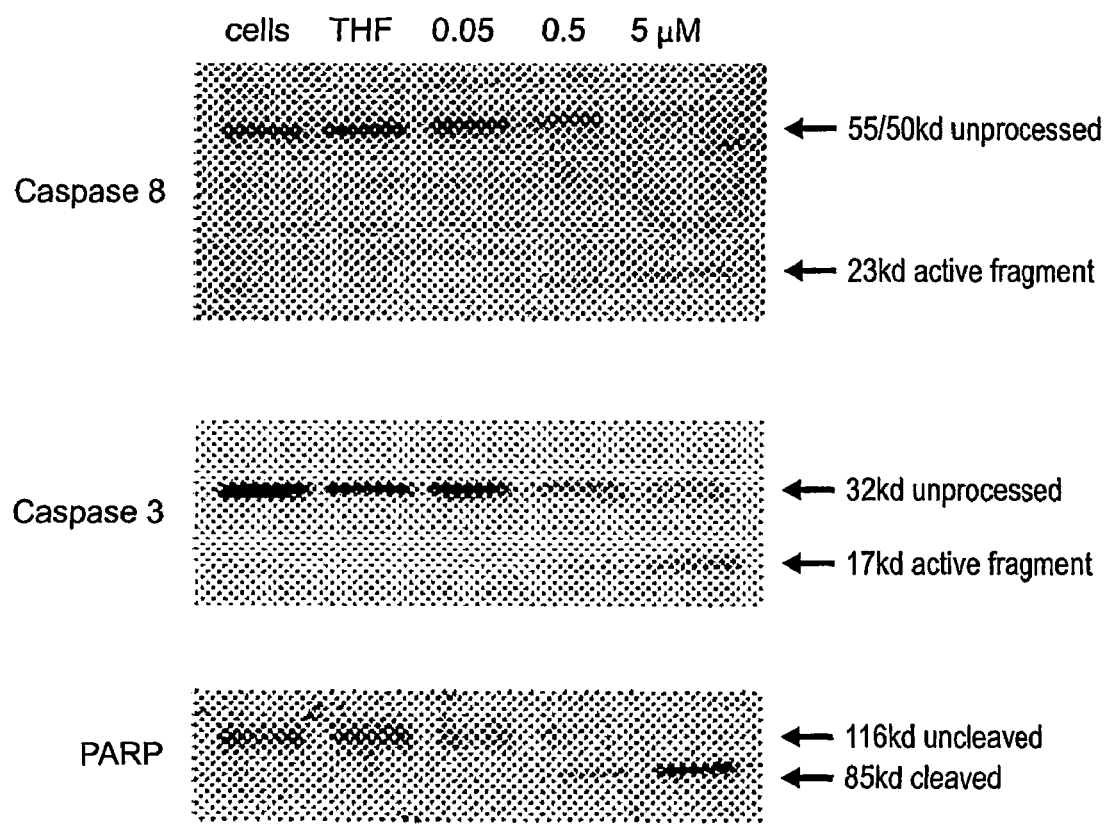

FIG. 3. Effect of 2-MeOE2bisMATE on caspase 8 and caspase 3 activation and PARP cleavage in Cal51 cells. Western blots showing caspase 8 and caspase 3 unprocessed and active fragments and PARP uncleaved and cleaved products following treatment of Cal51 cells with solvent, 0.05, 0.5 or 5 µM 2-MeOE2bisMATE for 48 hours.

Figure 4:
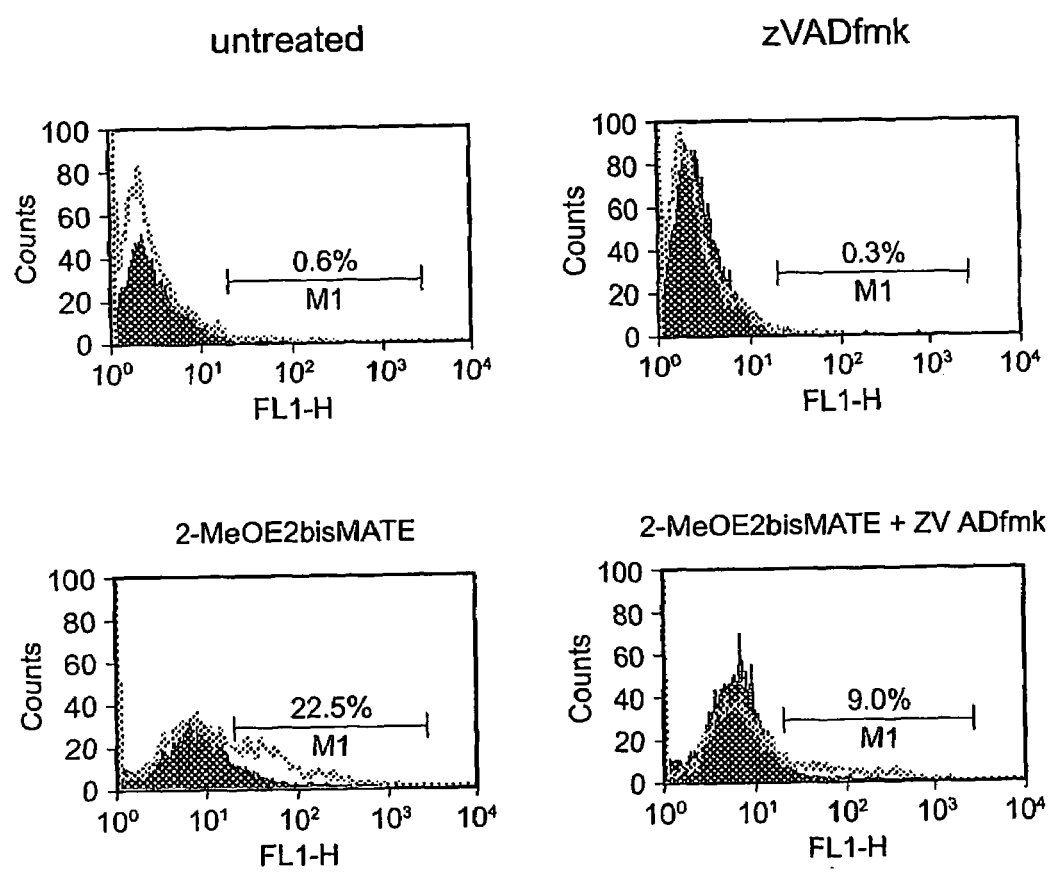

FIG. 4. Effect of the caspase inhibitor ZVAD-fmk on 2-MeOE2bisMATE induced apoptosis in Cal51 cells. TUNEL assay showing % apoptosis of cells untreated or following treatment with 50 µM ZVAD-fmk, 5 µM 2-MeOE2bisMATE or 5 µM 2-MeOE2bisMATE and 50 µM zVAD-fmk for 3 days. Histograms are overlays for control cells stained in the absence of TdT enzyme (bold) or cells stained with TUNEL reaction mix (open).

Figure 5:
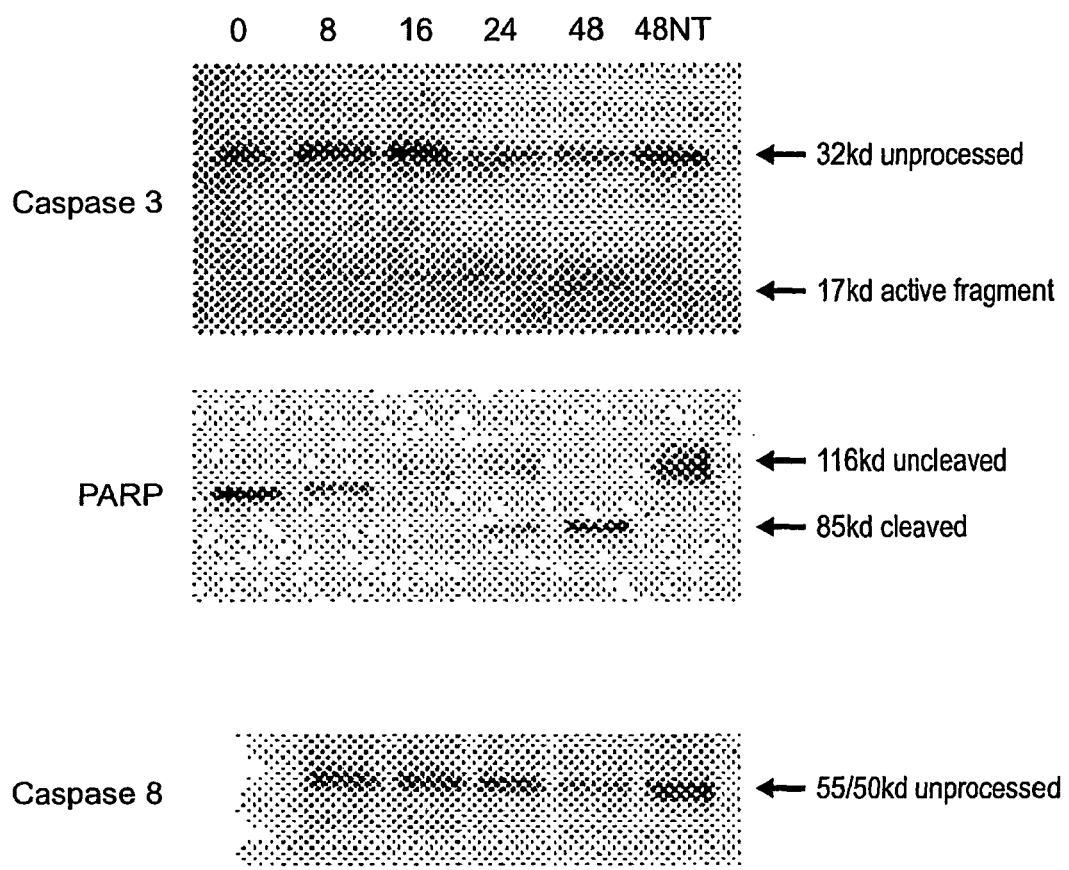

FIG. 5. Effect of 2-MeOE2bisMATE on the timing of caspase 3 and caspase 8 activation and PARP cleavage in Cal51 cells. Western blots showing caspase 3, caspase 8 and PARP unprocessed and cleaved products at 0, 8, 16, 24 and 48 hrs following treatment of Cal51 cells with 5 µM 2-MeOE2bisMATE for 48 hrs or untreated for 48 hrs (48NT).

Figure 6:
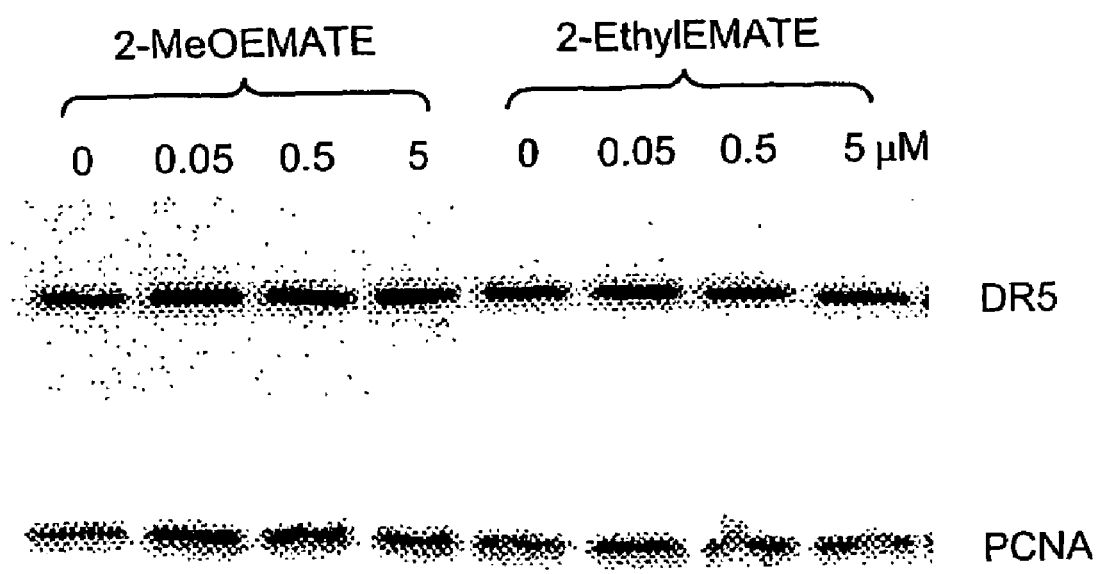

FIG. 6. Effect of 2-MeOEMATE and 2-EtEMATE on DR5 protein levels in Cal51 cells. Western blot showing DR5 protein levels following treatment of Cal51 cells for 48 hours with 0, 0.05, 0.5 and 5 µM of 2-MeOEMATE or 2-EtEMATE. PCNA levels represent corresponding loading controls.

Figure 7:
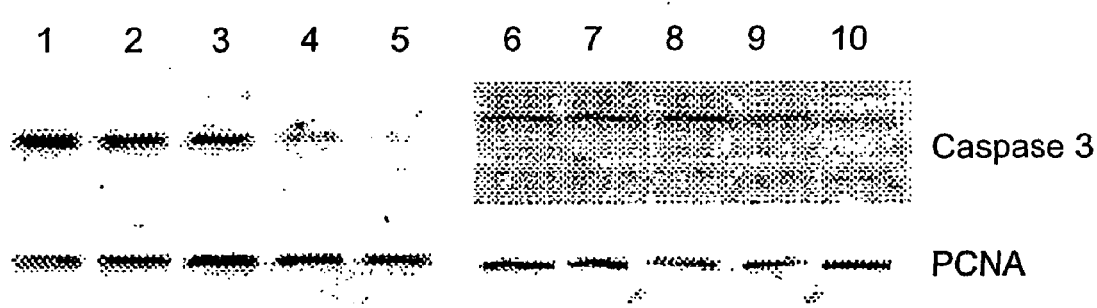
Figure 8:
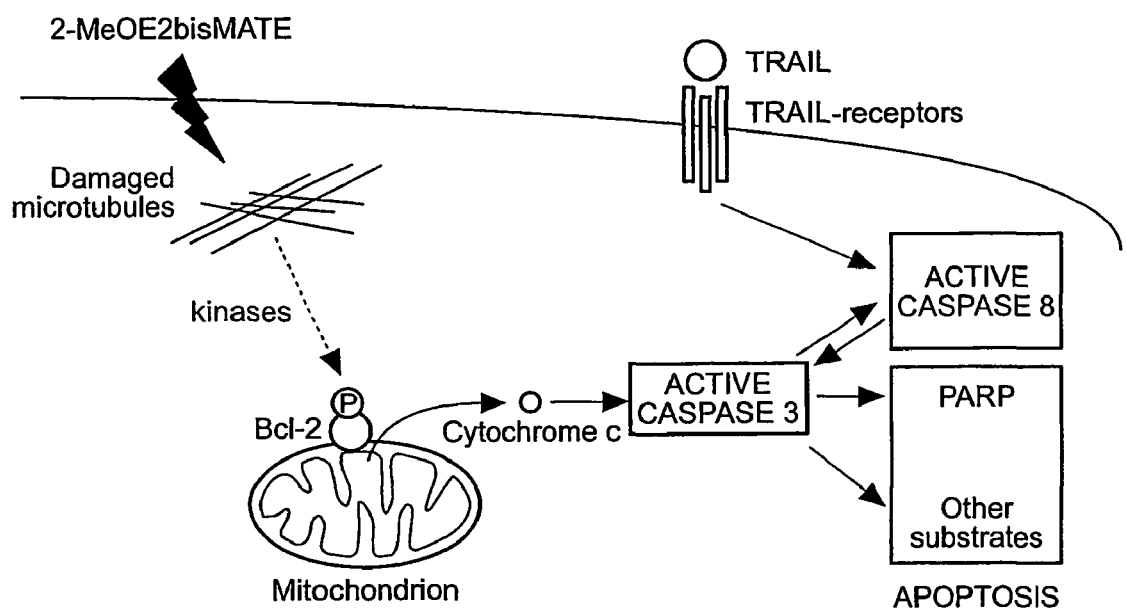

FIG. 7. Effect of combined treatment of 2-EtEMATE or 2-MeOEMATE and TRAIL on caspase 3 activation in Cal51 cells. Western blots showing caspase 3 activation following treatment of Cal51 cells for 48 hours with solvent, 250 ng/ml TRAIL and 5 µM 2-EtEMATE or 2-MeOEMATE in the presence or absence of 250 ng/ml TRAIL. PCNA levels represent corresponding loading controls. 1, control; 2, THF solvent; 3, TRAIL; 4, 2-EtEMATE; 5,2-EtEMATE+TRAIL; 6, control; 7, THF solvent; 8, TRAIL; 9, 2-MeOEMATE; 10, 2-MeOEMATE+TRAIL FIG. 8 shows a model for 2-MeOE2bisMATE induced cell killing. 2-MeOE2bisMATE induced apoptosis appears to be primarily dependent on mitochondrial mediated pathways activated by damaged microtubules rather than death receptors. However, these pathways can cooperate to potentiate cell killing via activation of caspase 3.

Figure 1A:
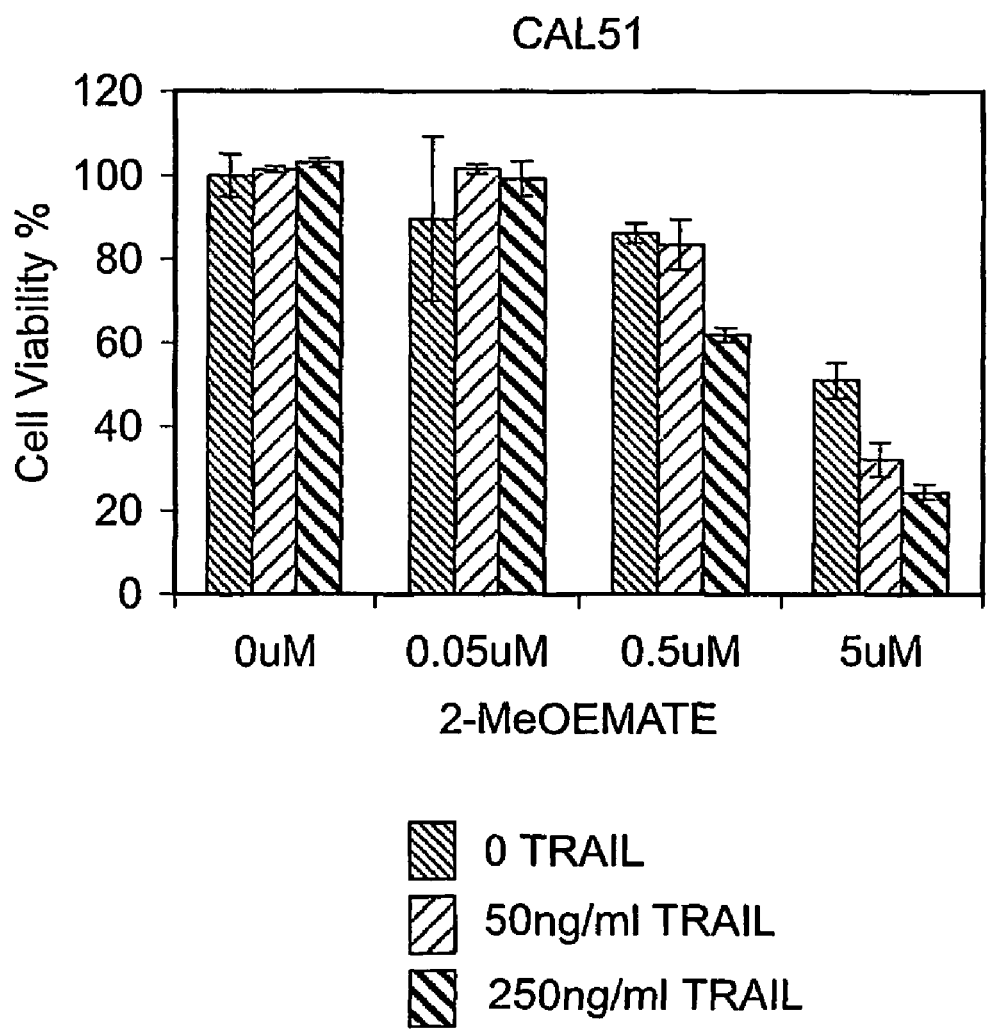
FIG. 1A shows a graph of the effect of 2-MeOEMATE on TRAIL induced apoptosis in CAL51 cells.
Figure 1B:
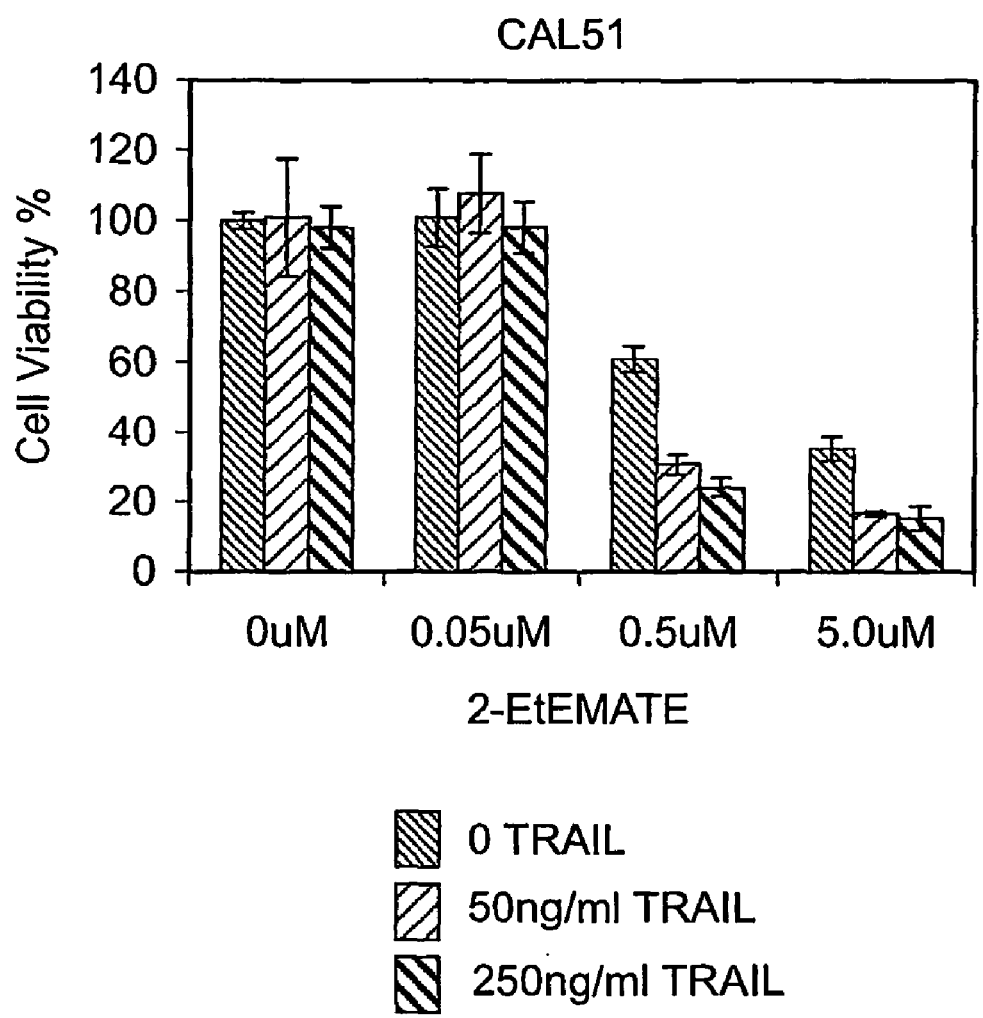
FIG. 1B shows a graph of the effect of 2-EtEMATE on TRAIL induced apoptosis in CAL51 cells.
Figure 1C:
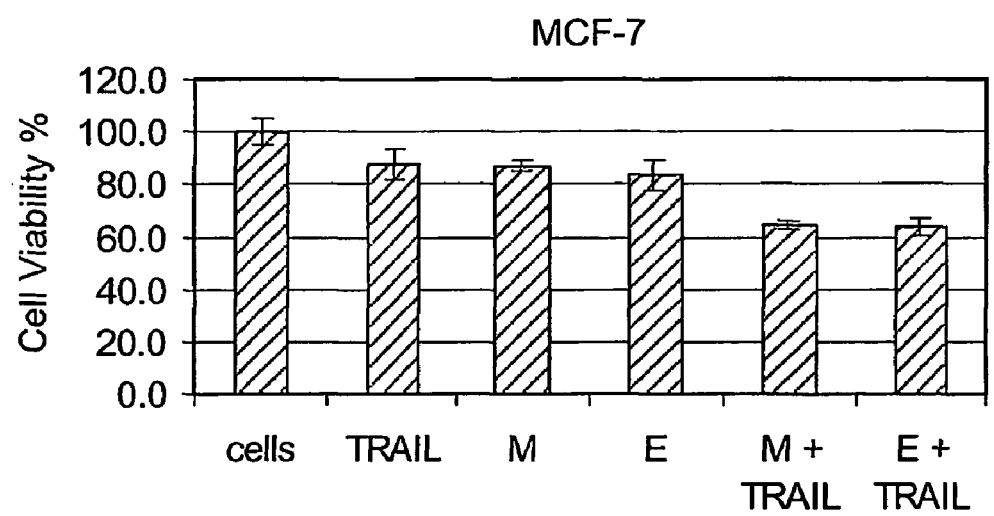
FIG. 1C shows a graph of the effect of 2-MeOEMATE and 2-EtEMATE on TRAIL induced apoptosis in MCF-7 cells at 24 hours.

FIGS. 1A to 1C show effects of 2-MeOEMATE and 2-EtEMATE on TRAIL induced apoptosis in CAL51 and MCF-7 cells. Cell proliferation assays in which CAL51 cells or MCF7 cells were plated at a density of 5,000 in 96 well plates and treated with 0, 0.05, 0.5 or 5 µM MeoEMATE or 2-EtEMATE in the presence of 0, 50 or 250 ng/ml recombinant human TRAIL. Results are the mean of triplicates+/− S.D. and are expressed as a percentage of results for untreated cells.

Figure 2:
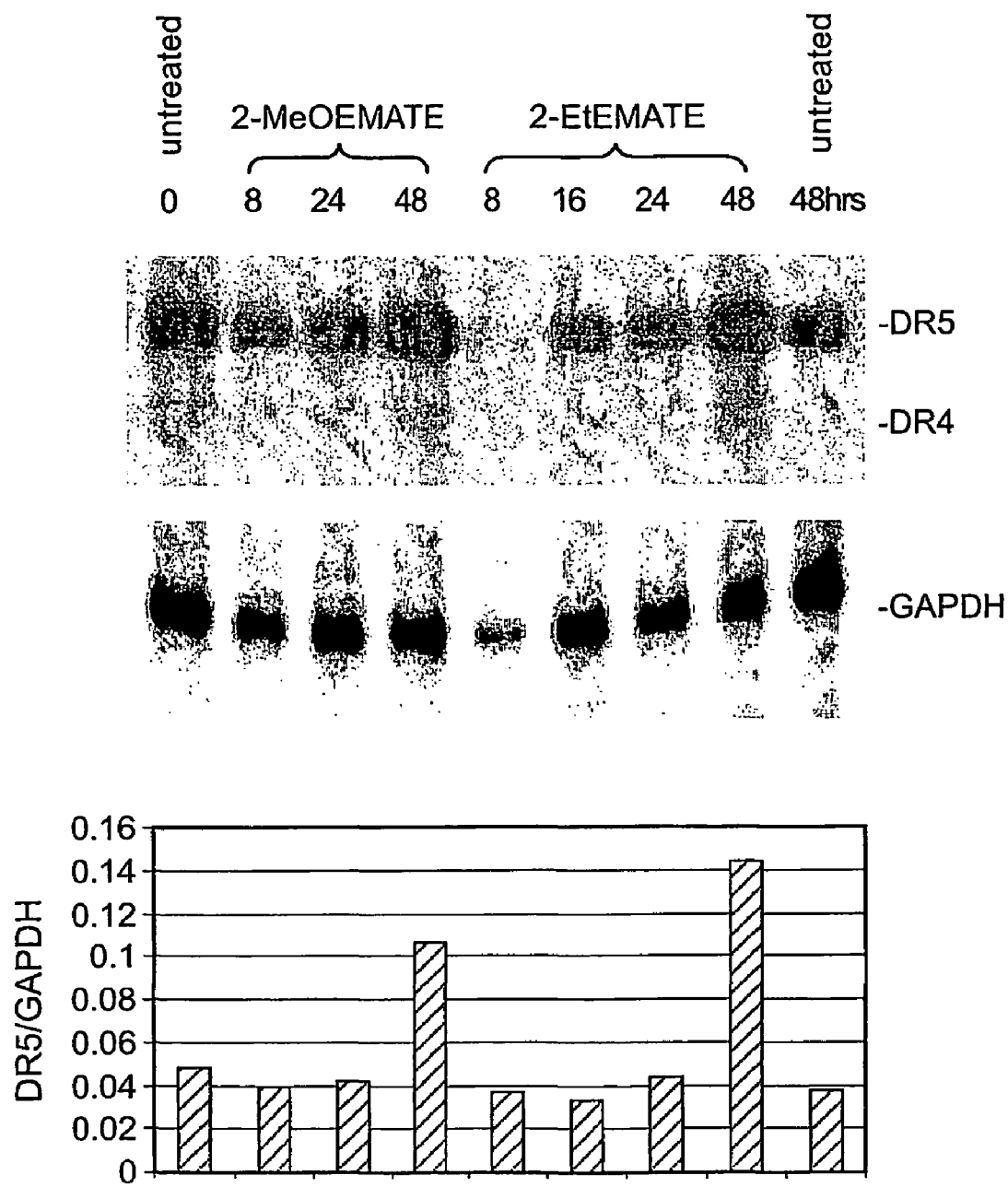
FIG. 2 shows a graph of the effect of 2-MeOEMATE and 2-EtEMATE on DR4 and DR5 mRNA levels in Cal51 cells.

FIG. 2 shows the effect of 2-MeOEMATE and 2-EtEMATE on DR4 and DR5 mRNA levels in Cal51 cells. RNAse protection assay showing DR5, DR4 and GAPDH mRNA levels at 0, 8, 16, 24 and 48 hours following treatment with 0.5 µM 2-MeOEMATE and 2-EtEMATE in Cal51 cells. Graph shows quantification of data from phosphoimager analysis of DR5 bands normalised by expression as ratio of DR5/GAPDH.

EXAMPLES

2-MeOEMATE and 2-EtEMATE were synthesised in accordance with the teachings of WO 99/64013 and WO 00/66095, respectively.

Example 1

We investigated if 2-MeOEMATE and 2-EtEMATE would co-operate with TRAIL to induce apoptosis in breast cancer cells. The data obtained are shown in FIGS. 1A to 1C.

Procedure

Cell proliferation was measured using the Cell Titre 96 Aqueous One Solution Cell proliferation assay (Promega). This is a colorimetric method which determines cell viability and can therefore be used to measure the ability of drugs to cause cell death. The assay is performed by adding the cell proliferation reagent directly to the cells. Metabolically active cells convert the reagent to a coloured formazan product and the absorbance at 490 nm is measured 1–4 hrs after incubation at 37° C.

For the TRAIL co-operation experiments, CAL-51 of MCF-7 cells were plated at 5,000 cells per well in 96 well plates. CAL-51 cells were treated with 0, 0.05, 0.5 or 5 µM 2-MeOEMATE or 2-EtEMATE in the presence of 0, 50 or 250 ng/ml recombinant human TRAIL. MCF7 cells were treated with 5 µM 2-MeOEMATE or 2-EtEMATE in the presence or absence of 250 ng/ml recombinant human TRAIL. Cell proliferation was measured 2 days (CAL-51) or 1 day (MCF-7) after addition of drugs. Tests were performed in triplicate and data are means of triplicate results+/–S.D. and are expressed as a percentage of results obtained for untreated cells. Experiments on CAL-51 cells were performed 4 times for each compound and once for each compound on MCF-7 cells.

Results

Treatment with 2-MeOEMATE or 2-EtEMATE alone induced up to 60% cell death in CAL51 cells over 2 days. When treated with TRAIL alone, CAL51 cells were resistant to TRAIL induced cell death. However, treatment with 2-MeOEMATE or 2-EtEMATE in combination with TRAIL in CAL51 cells enhanced the amount of cell death compared to treatment with 2-MeOEMATE or 2-EtEMATE alone. Treatment of MCF-7 cells with 2-MeOEMATE or 2-EtEMATE alone for 24 hrs induced 13% and 16% cell death. Treatment with TRAIL alone induced 12% cell death. However treatment with 2-MeOEMATE or 2-EtEMATE in combination with TRAIL enhanced the amount of cell death compared to treatment with the compounds alone (35% and 36%). Therefore the sulfamoylated derivatives sensitized CAL51 and MCF-7 cells to TRAIL induced apoptosis.

2-MeOEMATE and 2-EtEMATE enhance TRAIL induced apoptosis in Cal51 cells and MCF-7 cells.

Example 2

We investigated if the co-operation observed between TRAIL and 2-MeOEMATE or 2-EtEMATE to induce cell death in CAL51 cells was due to upregulation of DR4 and/or DR5 receptors by 2-MeOEMATE and 2-EtEMATE. We used RNAse protection assays to examine the levels of mRNAs for DR4 and DR5 following treatment of CAL51 cells with 2-MeOEMATE and 2-EtEMATE over 48 hours. The data obtained are shown in FIG. 2.

Procedure

This experiment was performed once. A radiolabeled RNA multi-probe was synthesised (Pharmingen RiboQuant Human Apoptosis Multiprobe template set hAPO-3c) using [$\alpha^{32}P$] UTP and 17 RNA polymerase. This multi-probe set allows simultaneous generation of several template probes for detection and measurement of apoptosis related genes. The set also includes probes for the housekeeping genes, L32 and GAPDH, which allows for normalisation of sampling and technique errors to permit comparison of mRNA levels between samples.

Total RNA was prepared using Trizol reagent (Gibco-BRL) from CAL-51 cells treated with 2-MeOEMATE or 2-EtEMATE for 0, 8, 16, 24 and 48 hrs. The radiolabelled multi-probe was hybridised to the RNAs overnight. The unhybridised RNA was digested with RNAse and the hybridised (protected) fragments were separated on a 6% acrylamide gel. The gel was dried and analysed by phosphoimaging on the Personal Molecular Imager Fx (Biorad). Protected fragment bands corresponding to DR5 and GAPDH were quantified and expressed as a ratio of DR5/GAPDH to normalise results.

Results

DR5 mRNA levels were significantly increased between 24 and 48 hours following treatment with both drugs compared to the untreated control. In contrast DR4 mRNA levels were low in comparison to DR5 levels and did not change significantly over this time period.

2-MeOEMATE and 2-EtEMATE upregulate DR5 receptor mRNA levels in CAL-51 cells.

Example 3

2-MeOE2bisMATE was synthesised in accordance with the teachings of WO 02/16392 (PCT/GB01/03688).

The above Examples demonstrate that 2-MeOEMATE or 2-EtEMATE overcame resistance to apoptosis induced by TRAIL. There is considerable interest in the therapeutic potential of TRAIL and we concluded that these compounds may be effective agents for enhancing TRAIL induced apoptosis in breast cancer therapies. We continued to analyse the molecular mechanisms of cell killing induced by 2-MeOEMATE and 2-EtEMATE, and extended the range of compounds studied to include 2-MeOE2bisMATE. We have focused on the role of caspases, sequence specific proteases that play a key function in apoptosis, and interactions with death receptor pathways. Although we have focused on results obtained using 2-MeOE2bisMATE, similar results were obtained with other sulfamoylated oestrogens.

Example 3.1

2-MeOE2bisMATE Activates Caspase 8 and Caspase 3 and Induces PARP Cleavage

Caspases play a central role in the execution of apoptosis by cleaving cellular proteins (e.g. PARP) resulting in many of the characteristic changes that occur when cells undergo apoptosis. There are more than a dozen caspases and some are associated with specific pathways of cell death. For example, activation of caspase 8 is associated with cell death induced via death receptors (e.g. receptors for TRAIL and Fas), whereas caspase 3 is a central mediator of cell death common to many pathways.

To determine whether caspases might play a role in cell death induced by 2-MeOE2bisMATE and other sulfamoylated oestrogen derivatives, we examined the expression of caspase 3, caspase 8 and PARP by immunoblotting (FIG. 3). Caspases are expressed as an inactive pro-form and their activation can be measured by the conversion to active enzyme. Treatment of Cal51 breast cancer cells with 2-MeOE2bisMATE induced a dose dependent activation of caspase 8 and caspase 3. Cleavage of PARP confirmed the activation of caspases in these cells. Therefore, cell death induced by the 2-MeOE2bisMATE in Cal51 cells is associated with caspase activation.

Example 3.2

Apoptosis Induced by 2-MeOE2bisMATE is Reduced by Caspase Inhibition

To determine whether the activation of caspases was important for cell killing, we tested whether a broad range chemical caspase inhibitor interfered with apoptosis. Cells were treated with 2-MeOE2bisMATE in the presence and absence of the caspase inhibitor ZVAD-fmk and cell death was analysed using the TUNEL assay which measures the DNA cleavage associated with apoptosis. The induction of TUNEL positive cells by 2-MeOE2bisMATE was reduced by 60% in the presence of zVAD-fmk (FIG. 4). Therefore 2-MeOE2bisMATE requires activation of caspases for optimal induction of apoptosis.

Example 3.3

2-MeOE2bisMATE Induced Caspase 3 Activation/PARP Cleavage Occurs Before Caspase 8 Activation There are two major pathways of apoptosis; cell surface death receptors activate caspases directly via activation of caspase 8 whereas other apoptotic stimuli operate via triggering the release of cytochrome c from mitochondria which subsequently activates caspases. Both pathways ultimately result in activation of caspase 3 and PARP cleavage. Since activation of caspase 8 is an indicator for the direct involvement of death receptors, it is important to determine whether activation of caspase 8 by 2-MeOE2bisMATE precedes or follows caspase 3 activation. We therefore performed time course experiments in Cal51 cells treated with 2-MeOE2bisMATE to order the activation events. Caspase 3 activation was first detected at 16 hours and as expected was followed by PARP cleavage at 24 hours (FIG. 5). Caspase 8 activation was a relatively late event, first detected at 48 hours. Therefore activation of caspase 3 induced by 2-MeOE2bisMATE precedes activation of caspase 8.

Example 3.4

2-MeOEMATE, 2-EtEMATE and 2-MeOE2bisMATE do not Upregulate DR5 Protein Levels by Western Blot in Cal51 Cells We previously demonstrated that the sulfamoylated oestrone derivatives upregulated DR5 mRNA in Cal51 cells providing a potential mechanism of their cooperative action. However, it was important to determine whether this change in RNA was also associated with increases in DR5 protein. Protein lysates were prepared from CAL51 cells treated with various compounds and analysed for expression of DR5 by immunoblotting (FIG. 6). In contrast to the results obtain from analysis of RNA, we did not detect a significant increase in DR5 protein levels by western blot following treatment of Cal51 cells for 48 hours with increasing concentrations of 2-MeOEMATE or 2-EtEMATE. We also observed no significant change in DR5 protein levels after treatment with 2-MeE2bisMATE for 48 hrs (not shown).

Example 3.5

Activation of Caspase 3 Induced by 2-MeOEMATE and 2-EtEMATE is Further Enhanced by Co-Treatment with TRAIL To further explore the mechanism for co-operation between sulfamoylated oestrones and TRAIL, we analysed activation of caspase 3 (FIG. 7). Treatment of Cal51 cells for 48 hours with 2-MeOEMATE or 2-EtEMATE induced activation of caspase 3 as detected by the reduction in levels of unprocessed caspase 3 by western blotting. Cal51 cells are resistant to TRAIL induced apoptosis treatment and there was no detectable caspase 3 activation when cells were treated with TRAIL alone. However when cells were treated with TRAIL in combination with 2-MeOEMATE or 2-EtEMATE activation of caspase 3 was further enhanced compared to treatment with either compound alone. Therefore, sulfamoylated oestrones and TRAIL cooperate to activate caspase 3.

SUMMARY

We have demonstrated that when used in combination with apoptosis inducers such as TRAIL, sulphamate compounds such as 2-MeOEMATE and 2-EtEMATE increase the sensitivity of breast cancer cells to apoptosis inducers. The mechanism for this increased sensitivity may involve the upregulation of receptor function, for example DR5 mRNA receptor function, induced by the sulfamoylated derivatives.

We have made considerable progress in understanding the molecular mechanisms of cell killing induced by the present compounds. These studies provide valuable information about how compounds such as 2-MeOE2bisEMATE exert their effects on cells, potential mechanisms of resistance and guidance for future screening. Our data support a model whereby mitochondrial events play a prominent role in cell killing. We have shown that caspase 3 is activated before caspase 8 and that inhibition of caspases interferes with cell death. Although we have not addressed the nature of the events occurring at the mitochondria which lead to caspase 3 activation, this may involve events already demonstrated to be associated with the actions of the sulfamoylated derivatives such as changes in the activities of BCL-2 family members that are located on the mitochondrial membrane (e.g. BCL-2 and BCL-XL phosphorylation), (MacCarthy-Morrogh et al 2000) or generation of reactive oxygen species (ROS) which can lead to mitochondrial damage and cytochrome c release (Wood et al 2002). The "late" activation of caspase 8 is probably downstream of caspase 3 and probably represents amplification of the apoptotic signal as a result of crosstalk between the pathways and may be mediated by caspase 6 which is also known to be activated by caspase 3 and has been reported to cleave caspase 8 (Slee et al 1999).

Although interfering with TRAIL and Fas death receptors does not prevent 2-MeOE2bisMATE-induced apoptosis it is possible to combine with death receptor stimulating agents to enhance cell killing. The synergistic effect of 2-MeOE2bisMATE and TRAIL is associated with increased activation of caspase 3. Rather than increased receptor expression, the molecular mechanism seems to involve sensitisation to the receptor signaling, for example, by inhibition of a signaling inhibitory molecule.

2-MeOE2bisMATE induced apoptosis appears to be primarily dependent on mitochondrial mediated pathways activated by damaged microtubules rather than death receptors. However, these pathways can cooperate to potentiate cell killing via activation of caspase 3.

Thus, in summary, the present invention provides a composition and compound suitable for use in the treatment of cancers and, especially, breast cancer.

In particular, in one aspect the present invention addresses the problem of blocking the growth of tumours in endocrine-dependent tissues (e.g. breast, endometrium, prostate). Nevertheless, other tumours (e.g. sarcomas, melanomas) should also be amenable to treatment with the composition and compound of the present invention.

It is also believed that the present invention has implications in treating hormonal conditions in addition to those associated with oestrogen. Hence, the present invention also provides a composition that is capable of affecting hormonal activity and is capable of affecting an immune response, wherein the composition is the composition of the present invention.

It is also to be understood that the composition of the present invention may have other important medical implications.

For example, the composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis, psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, sub-acute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

REFERENCES

Ashkenazi A and Dixit V M 1998 Science 281: 1305–1308
Chinnaiyan A M et al., 2000 Proc Natl Acad Sci USA 97: 1754–1759
Gibson S B et al., 2000 Mol Cell Biol 20: 205–12
Huang P et al., 2000 Nature 407 390–395
Keane M M et al., 1999 Cancer Res 59: 734–41
MacCarthy-Morrogh et al., 2000 Cancer Res 60: 5441–50
Wu G S et al., 1997 Nat Genet 17:141–143

The invention is further described by the following numbered paragraphs:

1. A composition comprising
   i) a compound comprising a sulphamate group ("a sulphamate compound"); and
   ii) an apoptosis inducer.
2. A composition according to paragraph 1 wherein the apoptosis inducer is an apoptosis inducing ligand.
3. A composition according to paragraph 1 wherein the apoptosis inducer is an apoptosis inducing cytokine.
4. A composition according to paragraph 1 wherein the apoptosis inducer is a tumour necrosis factor apoptosis inducing ligand (TRAIL).
5. A composition according to paragraph 4 wherein the TRAIL is TRAIL/Apo-2L.
6. A composition according to any one of the preceding paragraphs wherein the apoptosis inducer is capable of interacting with a tumour necrosis factor apoptosis inducing ligand (TRAIL) receptor.
7. A composition according to paragraph 6 wherein the receptor is DR4 and/or DR5.
8. A composition according to any one of the preceding paragraphs wherein the sulphamate compound is a cyclic compound.
9. A composition according to any one of the preceding paragraphs wherein the sulphamate compound is a polycyclic compound.
10. A composition according to paragraph 9 wherein the sulphamate compound is a compound having the formula:

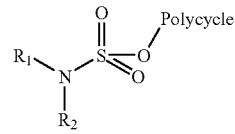

wherein each of $R_1$ and $R_2$ is independently selected from H or a hydrocarbyl group.
11. A composition according to any one of the preceding paragraphs wherein the sulphamate compound has a steroidal structure.
12. A composition according to paragraph 11 wherein the sulphamate compound is a compound having the formula:

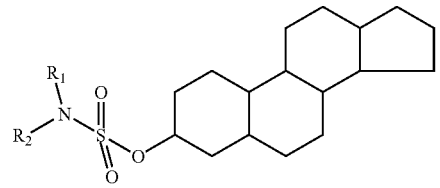

wherein each of $R_1$ and $R_2$ is independently selected from H or a hydrocarbyl group.
13. A composition according to paragraph 11 or 12 wherein the sulphamate compound has at least one sulphamate group attached to the 3 position of the A ring of the steroidal nucleus.
14. A composition according to any one of the preceding paragraphs wherein the sulphamate compound is substituted with a hydrocarbyl or an oxyhydrocarbyl group.
15. A composition according to paragraph 14 wherein the (oxy)hydrocarbyl group and the sulphamate group are each attached to the same ring at positions ortho with respect to each other.
16. A composition according to paragraph 15 wherein the sulphamate compound has a steroidal structure and the (oxy)hydrocarbyl group and the sulphamate group are each attached to the A ring of the steroidal structure.
17. A composition according to paragraph 16 wherein the (oxy)hydrocarbyl group is attached to the 2 position of the A ring of the steroidal structure.
18. A composition according to paragraph 16 or 17 wherein the sulphamate group is attached to the 3 position of the A ring of the steroidal structure.
19. A composition according to any one of paragraphs 14 to 18 wherein the oxyhydrocarbyl group is a group of the formula $C_{1-6}O$.
20. A composition according to paragraph 19 wherein the group $C_{1-6}O$ is a methoxy group.
21. A composition according to paragraph 1 wherein the sulphamate compound is 2-methoxyoestrone-3-O-sulphamate.
22. A composition according to any one of paragraphs 14 to 18 wherein the hydrocarbyl group is a group of the formula $C_{1-6}$.
23. A composition according to paragraphs 22 wherein the group $C_{1-6}$ is an ethyl group
24. A composition according to paragraph 1 wherein the sulphamate compound is 2-ethyloestrone-3-O-sulphamate.
25. A composition according to any one of the preceding paragraphs wherein the sulphamate group of the sulphamate compound has the formula:

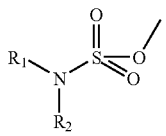

wherein each of $R_1$ and $R_2$ is independently selected from H or a hydrocarbyl group.

26. A composition according to any one of the preceding paragraphs wherein the sulphamate compound is suitable for use as an inhibitor of oestrone sulphatase (E.C. 3.1.6.2).

27. A composition according to any one of the preceding paragraphs wherein if the sulphamate group on the sulphamate compound were to be replaced with a sulphate group to form a sulphate compound then the sulphate compound would be hydrolysable by a steroid sulphatase enzyme (E.C.3.1.6.2).

28. A composition according to any one of the preceding paragraphs wherein if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 mM.

29. A composition according to any one of the preceding paragraphs wherein if the sulphamate group on the sulphamate compound were to be replaced with a sulphate group to form a sulphate compound and incubated with a steroid sulphatase enzyme (E.C.3.1.6.2) at a pH 7.4 and 37° C. it would provide a $K_m$ value of less than 50 μM.

30. A composition according to any one of the preceding paragraphs wherein the compound comprises at least two sulphamate groups.

31. A composition according to any one of the preceding paragraphs wherein the compound is steroidal and comprises at least two sulphamate groups.

32. A composition according to any one of the preceding paragraphs, wherein the composition further comprises a pharmaceutically acceptable carrier, diluent, or excipient.

33. A composition according to any one of the preceding paragraphs for use in medicine.

34. Use of a composition according to any one of the preceding paragraphs in the manufacture of a medicament to prevent and/or inhibit tumour growth.

35. Use of a composition according to any one of the preceding paragraphs in the manufacture of a medicament to induce apoptosis.

36. Use of a composition according to any one of the preceding paragraphs in the manufacture of a medicament to activate a caspase.

37. Use according to paragraph 36 wherein the caspase is caspase 3.

38. Use of a sulphamate compound in the manufacture of a medicament to upregulate receptor function of a tumour necrosis factor apoptosis inducing ligand (TRAIL) receptor.

39. Use according to paragraph 38 wherein the receptor is DR4 and/or DR5.

40. Use according to paragraph 38 or 39 wherein the sulphamate compound is a compound defined in any one of paragraphs 1 to 31.

41. Use of a sulphamate compound in the manufacture of a medicament to activate a caspase.

42. Use according to paragraph 41 wherein the caspase is caspase 3.

43. Use according to paragraph 41 or 42 wherein the sulphamate compound is a compound defined in any one of paragraphs 1 to 31.

44. A method of treatment comprising administering to a subject in need of treatment a composition according to any one of the paragraphs 1 to 31.

45. A method of treatment comprising administering to a subject in need of treatment a composition according to any one of paragraphs 1 to 31 or a sulphamate compound in order to induce apoptosis.

46. A composition substantially as described herein with reference to any one of the Examples.

47. A use substantially as described herein with reference to any one of the Examples.

48. A method substantially as described herein with reference to any one of the Examples.

We claim:

1. A composition comprising
i) a sulphamate compound having the formula

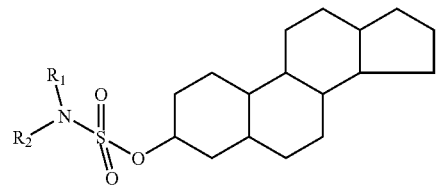

wherein each of $R_1$ and $R_2$ is independently selected from H or a hydrocarbyl group, and wherein an (oxy)hydrocarbyl group is attached to the 2 position of the A ring of the steroidal structure; and
ii) an apoptosis inducer
wherein the apoptosis inducer is a tumour necrosis factor-related apoptosis inducing ligand that binds to TRAIL-R1 or TRAIL-R2.

2. The composition according to claim 1, wherein the ligand is TRAIL/Apo-2L.

3. The composition according to claim 1, wherein the apoptosis inducer is capable, of interacting with a tumour necrosis factor-related apoptosis inducing ligand receptor.

4. The composition according to claim 1, wherein the (oxy)hydrocarbyl group is a group of the formula $C_{1-6}O$.

5. The composition according to claim 4, wherein the group of the formula $C_{1-6}O$ is a methoxy group.

6. The composition according to claim 1, wherein the sulphamate compound is 2-methoxyoestrone-3-O-sulphamate.

7. The composition according to claim 1, wherein the hydrocarbyl group is a group of the formula $C_{1-6}$.

8. The composition according to claim 7, wherein the group of the formula $C_{1-6}$ is an ethyl group.

9. The composition according to claim 1, wherein the sulphamate compound is 2-ethyloestrone-3-O-sulphamate.

10. The composition according to claim 1, wherein the sulphamate compound is an inhibitor of oestrone sulphatase (E.C. 3.1.6.2).

11. The composition according to claim 1, wherein if the sulphamate group of the sulphamate compound were to be replaced with a sulphate group to form a sulphate compound, then the sulphate compound would be hydrolysable by a steroid sulphatase enzyme (E.C.3.1.6.2).

12. The composition according to claim 1, wherein if the sulphamate group of the sulphamate compound were to be replaced with a sulphate group to form a sulphate compound, and the sulphate compound were incubated with a steroid sulphatase enzyme (E.C.3.1.6.2) at pH 7.4 and 37° C., it would provide a $K_m$ value of less than 50 mM.

13. The composition according to claim 1, wherein if the sulphamate group of the sulphamate compound were to be replaced with a sulphate group to form a sulphate compound, and the sulphate compound were incubated with a steroid sulphatase enzyme (E.C.3.1.6.2) at pH 7.4 and 37° C., it would provide a Km value of less than 50 µM.

14. The composition according to claim 1, wherein the sulphamate compound comprises at least two sulphamate groups.

15. The composition according to claim 1, wherein the composition further comprises a pharmaceutically acceptable carrier, diluent, or excipient.

16. A composition according to claim 1 wherein the sulphamate compound has the formula

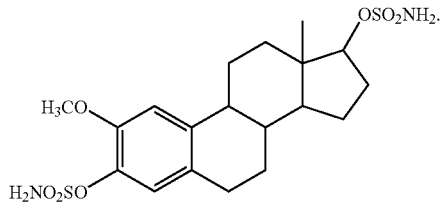

* * * * *

UNITED STATES PATENT AND TRADEMARK OFFICE
CERTIFICATE OF CORRECTION

PATENT NO.         : 7,211,246 B2
APPLICATION NO. : 10/728383
DATED                  : May 1, 2007
INVENTOR(S)       : Keith Graham Packham, Michael John Reed and Barry Victor Lloyd Potter It is certified that error appears in the above-identified patent and that said Letters Patent is hereby corrected as shown below:

Column 26, Claim 3, line 41: should read

3. The composition according to claim 1, wherein the apoptosis inducer is capable [[,]] of interacting with a tumour necrosis factor-related apoptosis inducing ligand receptor.

Column 28, line 15, please add Claim 17:

17. A composition according to claim 1 wherein the sulphamate compound has the formula

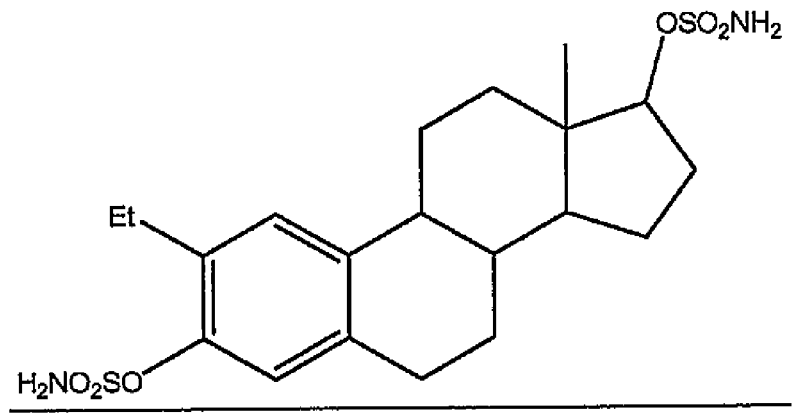

Signed and Sealed this

Twenty-seventh Day of November, 2007

JON W. DUDAS
*Director of the United States Patent and Trademark Office*